United States Patent [19]

Wallace

[11] Patent Number: 4,785,822
[45] Date of Patent: Nov. 22, 1988

[54] DISPOSABLE INTRACOMPARTMENTAL PRESSURE TRANSDUCER

[75] Inventor: William D. Wallace, Salt Lake City, Utah

[73] Assignee: Utah Medical Products, Inc., Midvale, Utah

[21] Appl. No.: 33,420

[22] Filed: Apr. 1, 1987

[51] Int. Cl.⁴ .............................................. A61B 5/02
[52] U.S. Cl. .................................. 128/675; 128/775; 128/786
[58] Field of Search ............... 128/642, 672, 673, 675, 128/748, 775, 784–786; 73/4 R, 708, 715, 721, 740

[56] References Cited

U.S. PATENT DOCUMENTS

| | | | |
|---|---|---|---|
| 3,710,781 | 1/1973 | Hutchins et al. | 128/675 |
| 4,136,681 | 1/1979 | Hon | 128/2 R |
| 4,191,193 | 3/1980 | Seo | 128/675 |
| 4,252,131 | 2/1981 | Hon et al. | 128/748 |
| 4,274,423 | 6/1981 | Mizuno et al. | 128/675 |
| 4,325,387 | 4/1982 | Helfer | 128/748 |
| 4,407,296 | 10/1983 | Anderson | 128/675 |
| 4,509,370 | 4/1985 | Hirschfeld | 73/705 |
| 4,576,181 | 5/1986 | Wallace et al. | 128/675 |
| 4,608,986 | 9/1986 | Beranek et al. | 128/786 |
| 4,610,256 | 9/1986 | Wallace | 128/675 |
| 4,611,600 | 9/1986 | Cohen | 128/675 |
| 4,640,983 | 2/1987 | Conte | 128/784 |
| 4,679,567 | 7/1987 | Hanlon et al. | 128/675 |
| 4,685,469 | 8/1987 | Keller | 128/675 |

OTHER PUBLICATIONS

"The Use of Catheter-Tip Pressure Transducers for the Measurement of Intrauterine Pressure in Labor-A Significant Advance.
"Intracardiac Catheter Tip Piezoresistive Pressure Gauge," The Review of Scientific Instruments, 31.9, 987–991 (1960).
"An IC Piezoresistive Pressure Sensor for Biomedical Instrumentation," EE Transactons on Biomedical Engineering, BME-20:2, 101–109 (1973).
"Millar Mikro-Tip Catheter Transducers," a company advertising brochure, 1–14.
"Catheter Tip Pressure Transducers," a company brochure prepared by Gaeltec.
Honeywell advertising brochure.
"A Stable Ultraminiature Catheter-Tip Pressure Transducer", (1973).
"The effect of oxytocin infusion on uterine activity levels in slow labor", British Journal of Obstetrics and Gynecology," (1985).
"Detection of the fetal ECG during labor by an intrauterine probe", Journal of Biomedical Engineering, (1988).

Primary Examiner—Max Hindenburg
Attorney, Agent, or Firm—Workman, Nydegger & Jensen

[57] ABSTRACT

A disposable pressure transducer apparatus for monitoring intracompartmental pressures, such as intrauterine and amniotic fluid pressures during childbirth. The apparatus includes a semiconductor pressure transducer mounted on a substrate. The substrate is secured within a flexible boot adapted to allow the pressure pulses present in a uterus to be communicated to the pressure transducer by way of a gel placed in aligned holes provided in both the substrate and the flexible boot.

A cable extends from the flexible boot to provide electrical connection between a semiconductor transducer and a monitor/display device. The cable is provided with an internal stiffening stylet to facilitate insertion of the boot into the uterus or other body compartment. The stylet is provided with a vent channel which communicates with the semiconductor transducer and extends along the cable to a hole in the plug on the distal end of the cable, to permit calibration and/or referencing of the transducer to atmospheric pressure.

22 Claims, 2 Drawing Sheets

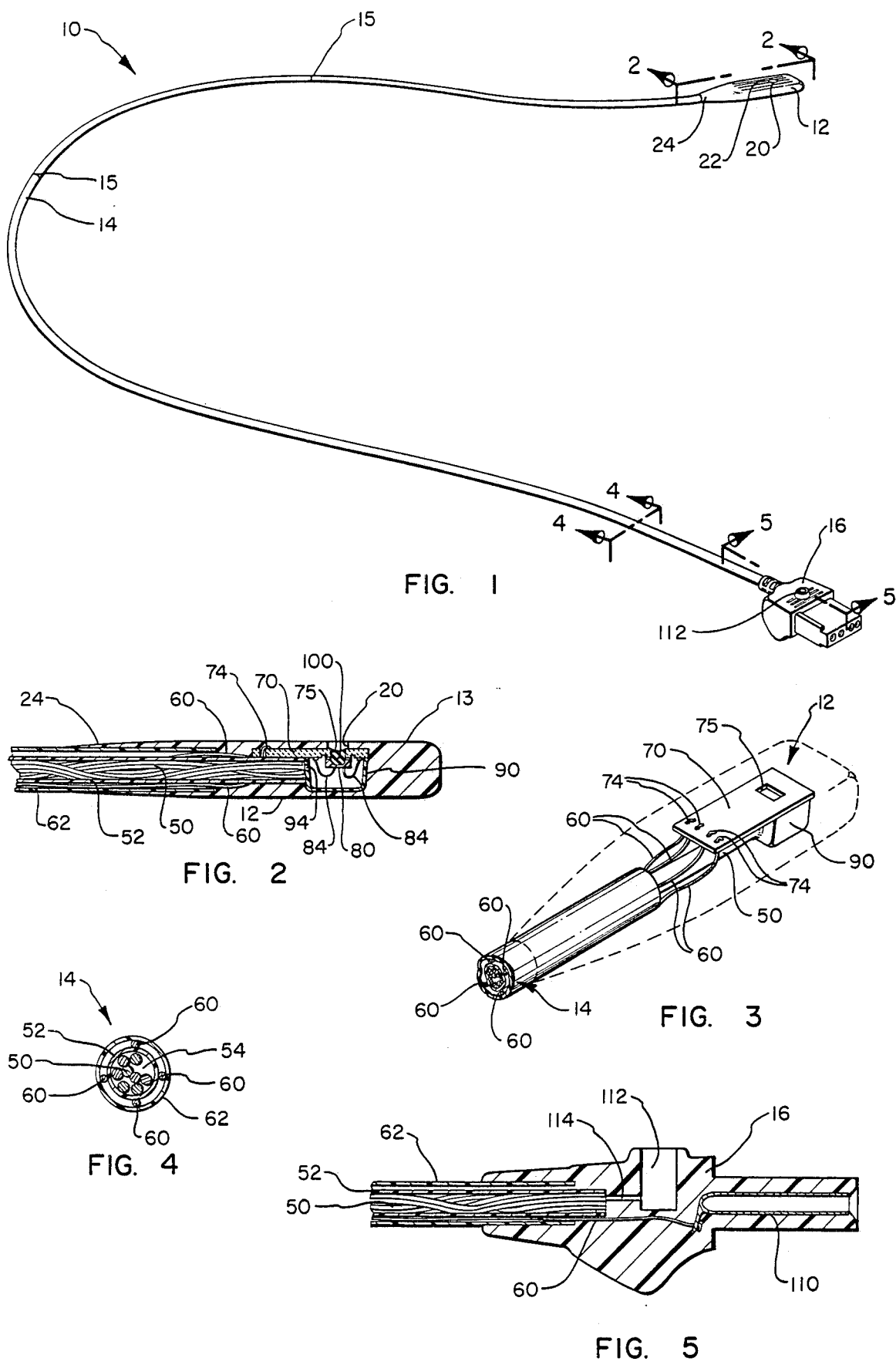

DISPOSABLE INTRACOMPARTMENTAL PRESSURE TRANSDUCER

BACKGROUND

1. The Field of the Invention

This invention relates to pressure transducers for medical use. More particularly, the present invention is directed to a novel, disposable pressure transducer apparatus for use in the direct measurement and/or monitoring of intracompartmental pressure, such as intrauterine pressure during labor and childbirth.

2. The Prior Art

There are many situations in which intracompartmental pressure monitoring may be useful, including intraarticular, esophageal, intra-intestinal and intracranial. Perhaps one of the most common type of intracompartmental pressure monitoring is intrauterine monitoring.

Each year, approximately 3.5 million children are born within the United States. In order to assist physicians in treating a mother and child approaching childbirth, monitoring devices are quite commonly used during the final stages of labor to monitor both the mother's uterine contractions and the fetal heart rate. Such monitoring devices can quickly provide the physician with information about the rate, duration, and intensity of the mother's uterine contractions and the effect of the contractions on the fetal heart rate. This information can held the physician ensure that oxygen and nutrients are being properly transferred from the mother to the fetus during labor and childbirth and can help the physician identify potential problems before they become life-threatening.

Most frequently, uterine contractions and the fetal heart rate are monitored using devices which can be secured externally to the surface of the mother's abdomen. For example, a pressure sensitive button called a tocotransducer is often secured to the mother's abdomen to provide information about the frequency and duration of the uterine contractions. The fetal heart rate may then be monitored by an ultrasound transducer, a phonotransducer, or some other suitable device.

In most cases, externally secured monitoring devices can provide sufficient information to enable a physician to treat the mother and child during labor and childbirth. It will be appreciated, however, that the use of external monitoring devices may give rise to large measurement errors in some cases due to extraneous noise and/or movement by the mother. In approximately ten percent of the childbirths, where there is a significant risk of complications, a physician may wish to have more accurate measurements than can be obtained using external monitoring devices.

In order to obtain more reliable and accurate information about the mother's uterine contractions, a physician will often initiate intrauterine pressure monitoring. In addition to providing information about the rate and duration of the uterine contractions, intrauterine pressure monitoring can also provide information about the intensity of the uterine contractions. Importantly, since the uterine pressure is being measured directly, errors in measurement due to extraneous noise and movement by the mother are less likely than with external monitoring devices.

One of the most widely used techniques for intrauterine pressure measurement and monitoring uses a fluid-filled catheter inserted into the uterus and then connected externally to a pressure transducer. In using this technique, a rigid guide tube is inserted just inside the mother's cervix. A special catheter is then threaded through the guide tube until it extends into the uterus approximately 15 to 20 centimeters (cm). This catheter is filled with some type of solution, such as, for example, a sterile saline solution. Once the catheter is in place, the guide tube is removed from the cervix and slid away from the mother along the catheter.

After the in-dwelling catheter is positioned as described above, the other end of the catheter is fluid coupled to a pressure transducer. The pressure transducer is then connected to some type of monitor device near the patient's bedside. Typical monitor devices include cathode ray tube display devices, digital display and/or recording devices, printers, and plotters.

In addition to the proper set-up of the measurement equipment in the above-described manner, it is also important to prime the catheter with a sterile solution so that any air bubbles within the catheter are removed and a continuous fluid column is provided from the pressure transducer to the tip of the catheter within the uterus. Then, when the mother's uterus thereafter contracts, the increased intrauterine pressure displaces the fluid within the catheter, and the pressure transducer detects a change in the intrauterine pressure. The pressure transducer generates electrical signals representing the intrauterine pressure, and such signals are then amplified and displayed by the monitor device. Usually, the monitor device is used to display the mother's intrauterine pressure as a function of time, along with the fetal heart rate, and this data can then be used by the physician and other medical personnel to appropriately diagnose and treat the mother and child.

While the foregoing technique for intrauterine pressure monitoring is widely used and can produce reliable measurements, there are a number of significant difficulties associated with this technique. First, the necessity of using a rigid catheter guide tube to insert the catheter into the uterus can make catheter insertion somewhat awkward and difficult, as well as posing a potential threat of puncturing a wall of the uterus and causing hemmorrhage, or causing injury to the child. Moreover, since the distal end of the catheter is typically secured to a needle or some other coupling device, it is difficult to remove the rigid guide tube from the catheter after the catheter is inserted. Often, the rigid guide tube makes it awkward to move the in-dwelling catheter around once it is inside the uterus of the patient, and the catheter may occasionally break, bend or become removed as a result of being pinched by the guide tube.

Another disadvantage of the above-described technique is that the fluid column necessarily opens into the uterus. As a result of fluid displacement in the catheter, amniotic fluid from the uterus invariably enters the catheter and may interfere with accurate pressure monitoring. Sometimes, an air bubble will also enter the catheter, or uterine tissue may obstruct the open end of the catheter. In such cases, it is necessary to flush the catheter with sterile solution to remove the air bubble or obstruction, and it may occasionally be necessary to replace the catheter altogether.

A further difficulty with the foregoing technique is due to the difficulty of zero balancing the pressure transducer to insure that the static readings it produces are accurate. A transducer is balanced in order to establish atmospheric pressure at the baseline or zero point from which the patient's intrauterine pressure is referenced.

A transducer is often used with a disposable dome that fits over the transducer diaphragm. The dome has two ports, one on the side and one vertical. The side port is connected to the in-dwelling fluid-filled catheter after it is primed with sterile solution. The other port is generally used for balancing and calibration.

In order to balance the transducer, the vertical port of the dome is opened to atmosphere and the other port is open to the catheter into the patient. The transducer is then raised or lowered until the top of the vertical port is level with the position of the in-dwelling tip of the fluid-filled catheter. For each inch off the proper level, there will be an error in the pressure reading of about 2 millimeters (mm) of mercury (Hg). The monitor is then zeroed and the transducer port recapped.

The difficulty in accurately balancing the transducer using the above-described technique for intrauterine pressure monitoring will be readily appreciated, since the tip of a catheter inside the mother's uterus cannot be seen. Consequently, the location of the tip of the catheter can only be estimated, and it is virtually impossible to determine whether the transducer is producing totally accurate pressure readings. One further disadvantage of the above-described system is that there are potential errors in the transducer readings that may be introduced as a result of overlying compliant tubing, or failure to adequately flush all air from the system prior to use. This will result in overdamping of the pressure readings.

It will be further appreciated that one of the most important components of an intracompartmental pressure monitoring system is the pressure transducer. Significantly, the accuracy and reliability of the pressure transducer set an upper limit to the quality of the pressure data which can be obtained. Therefore, those skilled in the art of pressure monitoring have attempted to develop pressure transducers which have a high degree of reliability, sensitivity, and accuracy.

Pressure transducers have typically been quite expensive to manufacture. Consequently, these transducers have often been provided in the form of a reusable instrument which can be connected to a fluid-filled catheter outside the patient by means of a disposable dome. Although such reusable pressure transducers can produce acceptable results, the use of such transducers has a number of significant disadvantages. First, since the transducer is to be used by a number of patients, the catheter and transducer dome must be sterilized for each use; and this sterilization procedure can be both time consuming and expensive. Further, the transducer must undergo periodic maintenance in order to assure its proper functioning and operation. All of these factors have made the use of reusable pressure transducers somewhat burdensome and inconvenient.

With the growth of the semiconductor industry and the recent developments in integrated circuit technology, disposable pressure transducers are increasingly used in place of conventional re-usable transducers. Nevertheless, these disposable pressure transducers also suffer from a number of disadvantages.

In order for a transducer to function properly, the diaphragm of the transducer must be vented on one side to a substantially constant pressure. Typically, one side of the diaphragm of the transducer is vented to atmospheric pressure. However, in intracompartmental applications such as intrauterine monitoring, when a transducer is positioned within the uterus or other body compartment, it can be extremely difficult to properly vent the transducer, and the lack of proper venting can make it very difficult to obtain accurate pressure measurements.

BRIEF SUMMARY AND OBJECTS OF THE INVENTION

In view of the foregoing problems experienced with prior art techniques for pressure monitoring as applied to intracompartmental monitoring, it is a primary object of the present invention to provide a disposable intracompartmental pressure transducer apparatus which is safer, more accurate and economical than prior art systems or apparatus.

It is also an object of the present invention to provide an apparatus for monitoring intracompartmental pressure which can be inserted, for example, inside a uterus, without the attendant problems associated with the use of a separate, rigid guide tube.

It is a further object of the present invention to provide an intracompartmental pressure monitoring apparatus which minimizes the risk of inaccurate pressure measurements due to interference of intracompartmental fluids, tissue and/or air bubbles entrapped in the system.

Another important object of the present invention is to provide an intracompartmental pressure transducer apparatus wherein one side of the diaphragm of the transducer is continuously vented to atmospheric pressure.

Additionally, it is an object of the present invention to provide an intracompartmental pressure transducer apparatus which can be readily calibrated not requiring rezeroing or balancing when the patient changes position even after the transducer has been inserted inside the uterus or other body compartment.

Consistent with these principal objects, the present invention is directed to a novel disposable pressure transducer apparatus for monitoring intracompartmental pressure. The apparatus comprises a pressure transducer having a pressure diaphragm. The pressure transducer is covered by a cap, and the cap is bonded to a stylet. The pressure transducer and cap are surrounded by a flexible boot. The flexible boot is provided with a hole which is positioned so as to communicate with the diaphragm of the pressure transducer, and the hole in the flexible boot is filled with a silicone gel such that pressure pulses may be transmitted through the silicon gel to the pressure transducer.

The stylet which is bonded to the cap covering the pressure transducer has a vent passageway therethrough. The vent passageway communicates through a hole in the cap with one side of the pressure transducer diaphragm. The stylet forms an integral part of the electrical cable which is used to connected the pressure transducer to a monitor device. The electrical cable has a plug which permits an apparatus to be attached to the cable so that a vacuum can be imposed on the backside of the transducer diaphragm through the vent passageway in the stylet, thereby facilitating calibration of the pressure transducer. The stylet is constructed with a stiffening member such that the catheter can be inserted without the use of guide tube. Further, the interstices of the stiffening membrane form the channel for the air vent to one side of the pressure transducer diaphragm.

The foregoing and other objects and features of the present invention will become more fully apparent from the following description and appended claims, taken in conjunction with the accompanying drawings.

BRIEF DESCRIPTION OF THE DRAWINGS

FIG. 1 is a perspective view illustrating one presently preferred embodiment of the disposable intracompartmental pressure transducer apparatus of the present invention.

FIG. 2 is a cross-sectional view of the pressure transducer apparatus taken along lines 2—2 of FIG. 1.

FIG. 3 is a perspective view illustrating the configuration of the pressure sensing components within the flexible boot of the apparatus, the flexible boot being shown by the broken lines.

FIG. 4 is a cross-sectional view of the electrical cable of the apparatus taken along lines 4—4 of FIG. 1.

FIG. 5 is a cross-sectional view of the plug on the electrical cable of the apparatus taken along lines 5—5 of FIG. 1.

DETAILED DESCRIPTION OF THE PREFERRED EMBODIMENT

Figure 6:
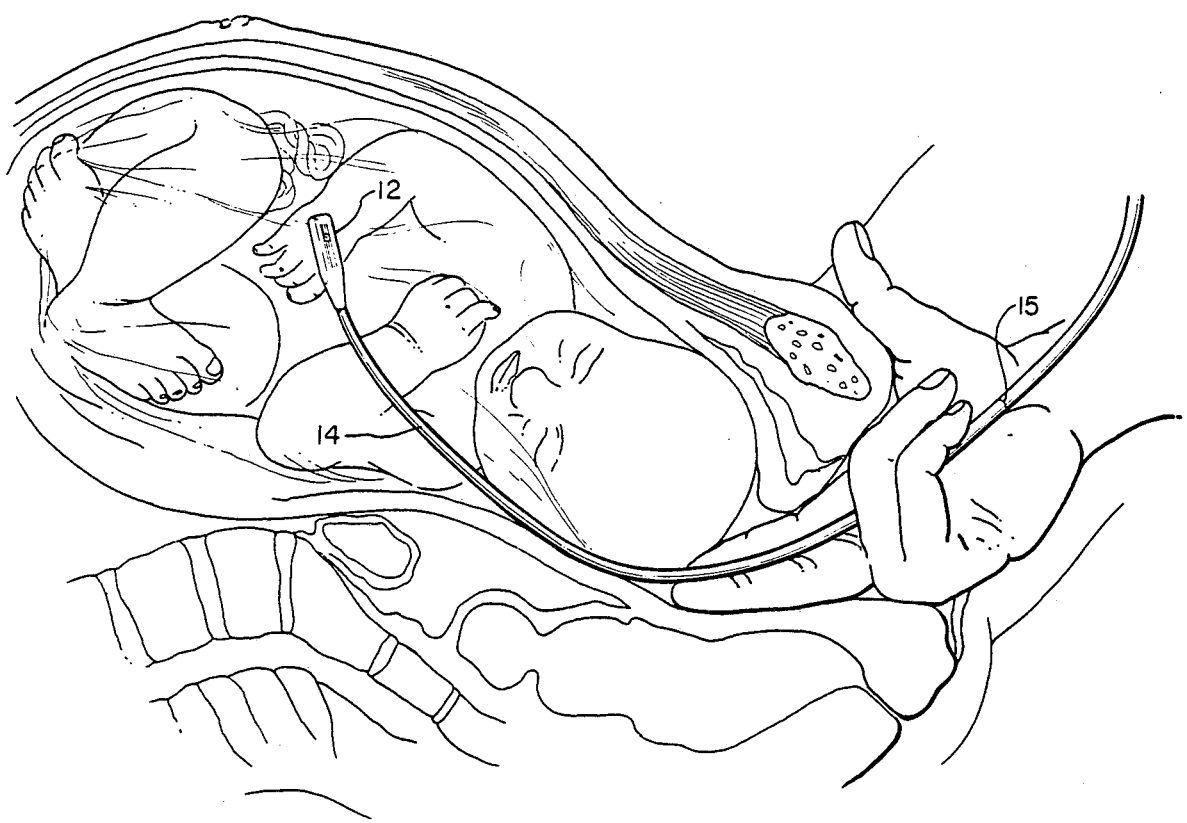
FIG. 6 is a perspective viewing illustrating placement of the transducer apparatus within a uterus to measure intrauterine pressure during childbirth.

It will be readily appreciated that the components of the present invention, as generally described and illustrated in the figures herein, could be arranged and designed in a wide variety of different configurations. As noted above, although particularly useful for measuring intrauterine pressure, the apparatus of the present may be adapted to a wide number of intracompartmental pressure monitoring applications, including but not limited to, intra-articular, esophageal, intra-intestinal and/or intracranial monitoring. Thus, the following more detailed description of the embodiment of the apparatus of the present invention, as represented in FIGS. 1 through 6, is not intended to limit the scope of the invention, as claimed, but it is merely representative of one presently preferred embodiment of the invention.

The presently preferred embodiment of the invention can be best understood by reference to the accompanying drawings, in which like parts are designated with like numerals throughout.

Referring first to FIG. 1, the various pressure sensing components of transducer apparatus 10, which will be described in more detail below, are contained within a flexible boot 12. As illustrated, boot 12 is provided with a hole 20 which communicates with the pressure sensing components. In addition, a cable 14 extends from boot 12 and serves to carry electrical signals which represent the pressure measurements made by transducer apparatus 10 to a monitor (not shown).

In use, the flexible boot 12 of transducer apparatus 10 is inserted into the uterus or other body compartment of a patient as shown in FIG. 6 and as more fully described hereinafter. The pressure detection components within boot 12 detect and measure the intracompartmental fluid pressure and generate electrical signals representing the pressure. The generated electrical signals are then transmitted along cable 14 to a plug 16, and plug 16 is connected to a monitor (not shown) such that the pressure data may be appropriately displayed and/or recorded.

One presently preferred embodiment for the pressure sensing components of transducer apparatus 10 is illustrated in FIGS. 2 and 3. As shown, these pressure sensing components comprise a pressure transducer 80 which is mounted on a substrate 70.

Pressure transducer 80 is formed by methods which are well-known in the art so as to include the required piezoresistive pressure diaphragm and measuring circuitry. For example, four resistive elements are ion-implanted on pressure transducer 80 so as to form a conventional Wheatstone bridge. In addition, a central portion of pressure transducer 80 is etched away (such as, for example, by chemical etching techniques), so as to form a piezoresistive diaphragm. If, for example, pressure transducer 80 is 0.020 inches (0.508 mm) thick, the central diaphragm of pressure transducer 80 could be formed so as to be approximately 0.0015 inches (0.0381 mm) thick.

As illustrated in FIGS. 2 and 3, substrate 70 has a hole 75 therethrough. Pressure transducer 80 is mounted to substrate 70 such that the piezoresistive diaphragm of pressure transducer 80 is positioned directly over hole 75 in substrate 70.

Pressure transducer 80 is mounted to substrate 70 such that thermal expansion and contraction of pressure transducer 80 will not subject pressure transducer 80 to mechanical stress which might cause incorrect, transient pressure readings. Thus, for example, pressure transducer 80 is secured with an adhesive material which is flexible enough to permit pressure transducer 80 to thermally expand and contract without significant interference. Such an adhesive may, for example, comprise a suitable silicone adhesive.

As depicted in FIG. 2, the central diaphragm of pressure transducer 80 is electrically connected to other circuitry on substrate 70 that is provided for purposes of temperature compensation as described further below. For example, solder pads may be provided on substrate 70, and the diaphragm of pressure transducer 80 can be electrically connected to the solder pads on substrate 70 by means of wires 84 or flex circuit solder bumps.

Substrate 70 may be formed of any of a number of suitable dielectric materials, such as, for example, a ceramic material. Substrate 70 is preferably provided with a conventional temperature compensation circuit which is used to adjust both the zero pressure point and the gain of transducer apparatus 10 such that these parameters will not change with variations in temperature. Such a temperature compensation circuit also determines the gain or sensitivity of transducer apparatus 10, such gain being typically on the order of approximately five microvolts per volt of excitation per millimeter of mercury pressure. Further, the temperature compensation circuit is used to match the input and output impedance of transducer apparatus 10 with that of the monitor device (not shown), typical impedances being about 350 ohms. This compensation can also be placed on the sensor 80 by using thin film processing.

A temperature compensation circuit may be provided on substrate 70 in any suitable manner. For example, the temperature compensation circuit may be provided using appropriate thick film silk-screening techniques. Thereafter, the various components of the temperature compensation circuit may be laser-trimmed to the required values by means which are known in the art.

Substrate 70 is also provided with a means for electrically connecting the circuitry on substrate 70 and pressure transducer 80 to the conductors 60 of cable 14. For example, substrate 70 may be provided with solder pads at 74, and conductors 60 may be connected to the solder pads at 74 in a conventional manner.

A cap 90 is secured to substrate 70 so as to cover pressure transducer 80. Cap 90 thus protects pressure transducer 80, together with the associated wires 84, from mechanical injury. Cap 90 is secured to substrate 70 by means of a suitable adhesive, such as, for example, a U.V. cure adhesive. The substrate 70, with associated compensation circuitry, with transducer 80 joined and electrically connected thereto, and cap 90 together comprise the basic transducer means for sensing intracompartmental fluid pressures.

The transducer means comprised of substrate 70, transducer 80, and cap 90 is housed within a protective flexible boot 12, which serves as a protective means of cushionings those components. Boot 12 may have virtually any suitable configuration which will allow for insertion of boot 12 into the uterus or other body compartment for which the apparatus is designed. In order to protect against injury, boot 12 is preferably formed of a soft flexible material, such as, for example, low durometer PVC or silicone (45 shore A), and boot 12 extends substantially beyond the end of substrate 70 and cap 90 to form a flexible cushion 13 at the leading end of the boot.

To protect the electrical components of transducer apparatus 10 from exposure to moisture within the uterus or other intracompartmental environment, the open end 24 of boot 12 is sealed in some manner to the outer insulation layer 62 of cable 14. Boot 12, may, for example, be vacuum formed or heat bonded around the end of cable 14. Alternatively, boot 12 can be secured to insulation layer 62 of cable 14 using a suitable waterproof adhesive.

Boot 12 is provided with a hole 20 which is positioned so as to be in alignment with hole 75 in substrate 70. As described further below, hole 20 permits pressure pulses to be transmitted through boot 12 so as to be detected by transducer 80. Advantageously, in order to prevent fluids or tissue from obstructing hole 20 and thus interfering with the pressure measurements, boot 12 may be provided with a plurality of grooves 22 surrounding hole 20, as illustrated in FIG. 1.

As shown in FIG. 2, hole 20 in boot 12 and hole 75 in substrate 70 can be filled with a suitable dielectric material 100, such as, for example, a gel material. Gel material 100, which fills the holes 75 and 20 of substrate 70 and boot 12 provides a means for hydraulically coupling the diaphragm of transducer 80 to intracompartmental fluids so that the fluid pressure can thereby be transmitted to transducer 80 and sensed. Gel 100 may comprise a silicone gel. Gel 100 also forms a fluid-tight seal between boot 12 and substrate 70 and electrically isolates substrate 70 and its associated circuitry from the amniotic or other body fluids surrounding the transducer. This increases the safety of the device by helping to minimize any electrical shock hazard to the patient.

The structure and method of manufacturing the presently preferred pressure sensing components of transducer apparatus 10, which are described above, are further set forth in U.S. Pat. No. 4,576,181, issued Mar. 18, 1986 for DISPOSABLE PRESSURE TRANSDUCER APPARATUS FOR MEDICAL USE, which is incorporated herein by reference.

In order to facilitate insertion of boot 12 into the uterus or other body compartment of a patient, cable 14 is preferably provided with a stiffener means which, in the preferred embodiment, is comprised of stylet 50 (see FIGS. 2 and 3). The use of a stylet 50 in cable 14 obviates the need for using a rigid guide tube of some sort as must be used with conventional intrauterine pressure sensing techniques, so that the cable 14 can be used for insertion of the transducer. In addition, the interstices of the stylet forms a vent space 54. Cable 14 can be provided with a stylet 50 in any of a number of different ways. One presently preferred configuration for a cable 14 which includes a suitable stylet 50 is illustrated in FIG. 4.

As shown, cable 14 comprises a stranded steel stylet 50 which is surrounded by an insulating sheath 52. Conductors 60 of cable 14 are positioned on the outside of insulating sheath 52, as shown.

Conductors 60 may be any suitable electrical conductors. For example, conductors 60 may be magnet wire conductors. Advantageously, since magnet wires are typically already insulated, they do not require a separate insulation coating. To provide further insulation and a smooth outer surface to cable 14, an outer insulating sheath 62 is provided. Thus, the overall cable means of the apparatus is comprised of stylet 50, insulating layer or sheath 52, conductors 60 and outer insulation layer or sheath 62.

In order to obtain accurate pressure measurements, the pressure readings of transducer apparatus 10 should be referenced to some substantially constant pressure. This may easily be done by using a vent means to reference the pressure readings to atmospheric pressure. To this end, the interior of cap 90 surrounding transducer chip 80 is continuously vented to atmospheric pressure by means of a vent channel 54 (see FIG. 4) in cable 14. The vent channel 54 communicates both with the interior of cap 90, through a vent hole 94 (FIG. 2) in cap 90 and with the atmosphere through a suitable vent port 112 (FIGS. 1 and 5) located somewhere along cable 14, such as, for example, in a plug 16 at the end of cable 14. Thus, by providing an air passageway to and from cap 90, the vent channel 54 of cable 14 assures that the side of the transducer diaphragm covered by cap 90 is continuously referenced to atmospheric pressure.

The vent channel 54 may be provided in cable 14 in a number of different ways. Some of the ways for providing a suitable vent channel in cable 14 are set forth in the above-referenced patent. For purposes of the present invention, it is presently preferred that the vent channel in cable 14 be provided by means of the stylet 50 in cable 14.

As discussed previously and illustrated in FIG. 4, stylet 50 may comprise a cable having multiple strands of steel wire. In such case, the vent channel 54 in stylet 50 may be provided by removing one of the steel wires from stylet 50. Stylet 50 may then be bonded to cap 90, as depicted in FIG. 2, so that the vent channel 54 in stylet 50 communicates through vent hole 94 with the interior of cap 90.

The distal end of cable 14 is provided with a suitable connector, such as, for example, a plug 16. Plug 16 may be formed of any suitable material, for example, a plastic material prepared by means of injection molding or by other means which are well-known in the art. Plug 16 may then be bonded by means of an adhesive or by means of heat-bonding to the external insulative sheath 62 of cable 14.

As depicted in FIG. 5, the conductors 60 of cable 14 are electrically connected to contacts 110 within plug 16. Contacts 110 may then be coupled to appropriate leads such that conductors 60 can be properly connected to a monitor/display device.

A hole 112 is formed in plug 116 and communicates with a bore 114, as shown in FIG. 5. Bore 114 communicates with vent channel 54 (see FIG. 4) of stylet 50. Thus, since space 54 communicates with the interior of cap 90, as described above and illustrated in FIG. 2, the interior of cap 90 is continuously vented to atmospheric pressure through space 54 and stylet 50, together with bore 114 and hole 112 in plug 16.

Advantageously, hole 112 can also be used to calibrate the pressure monitoring system. For example, a vacuum can be imposed through hole 112, bore 114, and vent channel 54 in stylet 50 on the backside of transducer 80 within cap 90. Since transducer 80 is a true differential device, a vacuum on the backside of the diaphragm of transducer 80 is completely equivalent to a pressure on the patient's side of the transducer. The method for calibrating the pressure monitoring system using hole 112 in plug 16 is disclosed more fully in U.S. Pat. No. 4,610,256, issued Sept. 9, 1986 for PRESSURE TRANSDUCER, which is incorporated herein by reference.

The manner in which transducer apparatus 10 may be used is illustrated, for example, in FIG. 6, which shows an intrauterine application. The patient should be in the dorsal lithotomy position, the uterine membrane ruptured and the cervix adequately dilated. Using the hand and fingers as shown to guide the apparatus, it is inserted into the cervix until it is well into the amniotic space for intrauterine monitoring. Insertion should be performed carefully and gently, without force. Any cervical quadrant may be used. Stylet 50 of cable 14 must have a desired rigidity so that the intrauterine monitoring, the apparatus will accommodate insertion of the boot 12 past the fetal head while manipulating the apparatus from outside the introitus. Importantly, since the transducer is inside the patient at the catheter tip, zeroing is not a problem, and attendant inaccuracies in this regard are eliminated since the transducer is positioned at the desired reference level.

If desired, markings 15 (see FIG. 1) may be placed on cable 14 at suitable intervals (for example, one mark at 12 inches and two marks at 18 inches), to assist the physician or nurse in determining depth of insertion. Total length of the apparatus is approximately 3 feet (80 cm), with the flexible boot containing the transducer being about 0.35" (0.77 cm)×0.2" (0.44 cm)×0.61" (1.34 cm). The cable 14 with stylet 50 is preferrably about 0.160" (0.41 cm) wide.

Since cable 14 of transducer apparatus 10 includes a stiffening stylet 50, transducer apparatus 10 can be inserted into the uterus without the use of a rigid guide tube as required with conventional intrauterine pressure monitoring techniques. Further, since the present invention does not require the use of a fluid-filled catheter inserted into the uterus, the present invention does not suffer from the disadvantages associated with amniotic fluid or air bubbles entering the catheter, or the problem of continuously balancing the zero of the transducer.

Boot 12 of transducer apparatus 10 is also designed so as to increase safety by providing a soft cushion at the tip of the catheter, as well as preventing obstruction by intrauterine tissue. Specifically, grooves 22 on the surface of boot 12 prevent intrauterine tissue from sealing hole 20 and interfering with accurate pressure measurements.

The semiconductor transducer 80 of transducer apparatus 10 is continuously vented to atmosphere through a vent channel formed in stylet 50 which extends along the length of cable 14 of transducer apparatus 10 to a hole in plug 16 on cable 14. Advantageously, the vent channel can also be used to calibrate the semiconductor transducer directly using a known pressure source, even when the transducer is inside the uterus or other body compartment.

The invention may be embodied in other specific forms without departing from its spirit or essential characteristics. The described embodiments are to be considered in all respects only as illustrative and not restrictive. The scope of the invention is, therefore, indicated by the appended claims, rather than by the foregoing description. All changes which come within the meaning and range of equivalency of the claims are to be embraced within their scope.

What is claimed and desired to be secured by United States Letters Patent is:

1. An intracompartmental pressure transducer apparatus, comprising:
   a pressure transducer having a diaphragm with first and second sides;
   a protective cushion means for enclosing said pressure transducer therein;
   means for communicating pressure pulses to the first side of said diaphragm through said protective cushion means;
   means for venting the second side of said diaphragm to atmospheric pressure; and
   electrical cable means for electrically connecting the pressure transducer to a monitor device for displaying data corresponding to intracompartmental pressure sensed by said pressure transducer, said electrical cable means having a leading end adapted for insertion into a body compartment, said pressure transducer and said protective cushion means being mounted at said leading end, said electrical cable means further comprising stiffener means premanently encased in said electrical cable means for imparting a desired degree of rigidity to said electrical cable means to facilitate intracompartmental insertion of said transducer using said electrical cable means.

2. An apparatus as defined in claim 1 wherein the pressure transducer comprises a semiconductor chip having a piezoresistive pressure diaphragm.

3. An apparatus as defined in claim 2 further comprising a dielectric substrate, said substrate having a hole formed therethrough, and wherein the pressure transducer is mounted on said substrate such that the first side of the pressure diaphragm is positioned over said hole.

4. An apparatus as defined in claim 3 wherein the protective cushion means comprises a flexible boot surrounding the pressure transducer, and wherein the means for communicating pressure pulses comprises a hole formed through the boot which communicates with the hole formed through said substrate and over which the first side of the pressure diaphragm is mounted.

5. An apparatus as defined in claim 4 wherein the pressure communicating means further comprises a dielectric material which substantially fills the holes in the flexible boot and substrate so as to be in contact with the first side of the pressure diaphragm and so as to hydraulically couple said first side of the diaphragm to intracompartmental fluids.

6. An apparatus as defined in claim 4 wherein the flexible boot has a plurality of grooves formed therein adjacent said hole formed through the boot, said grooves serving to prevent clogging of the hole in said boot by tissue.

7. An apparatus as defined in claim 1 wherein the cable means comprises a plurality of wires electrically connected to the pressure transducer and encased within an insulative sheath.

8. An apparatus as defined in claim 7 wherein the means for venting comprises a vent space formed in association with said cable means so as to be in communication with the second side of the pressure diaphragm.

9. An apparatus as defined in claim 8 further comprising a cap positioned over the pressure transducer so as to enclose the second side of the pressure diaphragm.

10. An apparatus as defined in claim 9 wherein the means for venting further comprises a vent hole formed through a side of said cap and in communication with the vent space formed through the cable means.

11. An apparatus as defined in claim 10 further comprising a plug connected to the cable means, the plug having a channel formed therethrough in communication with the vent space formed through the cable means.

12. An apparatus as defined in claim 11 wherein said channel of the plug terminates at one end in a hole formed in a side of the plug.

13. An apparatus as defined in claim 1 wherein said stiffener means comprises a plurality of wires encased within said cable means.

14. A transducer apparatus for measuring intracompartmental fluidic pressures, said apparatus comprising:
   a pressure transducer means for converting pressure into a proportional electrical signal, said pressure transducer means comprising a diaphragm with first and second sides;
   a protective cushion means for enclosing said pressure transducer means therein, said protective cushion means comprising a resilient material;
   means formed in said cushion means for hydraulically coupling said transducer diaphragm through said cushion means to intracompartmental fluids so as to apply said intracompartmental fluidic pressures to said first side of said diaphragm;
   cable means for electrically connecting said pressure transducer means to an output monitor, said cable means comprising leading and trailing ends, and vent means for introducing atmospheric pressure to said second side of said diaphragm, said cable means being joined to said pressure transducer means and to said cushion means at said leading end for insertion into a body compartment, and said cable means further comprising stiffener means encased therein for imparting a desired degree of rigidity to said cable means to facilitate intracompartmental insertion of said pressure transducer means using said cable means.

15. An apparatus as defined in claim 14 wherein said pressure transducer means comprises substrate means onto which said diaphragm is mounted, and cap means joined to said substrate means so as to form a protective cover over said diaphragm.

16. An apparatus as defined in claim 15 wherein said hydraulic coupling means comprises a dielectric material and openings formed through said substrate means and said cushion means for receiving and holding said dielectric material adjacent to said first side of said diaphragm.

17. An apparatus as defined in claim 16 wherein said cushion means comprises an elongated boot with grooves formed on one surface thereof adjacent the opening formed through said cushion means, said grooves serving to prevent clogging of said opening by tissue.

18. An apparatus as defined in claim 14 wherein said cable means comprises a first insulation layer and a plurality of first wires encased therein and electrically connected to said transducer means.

19. An apparatus as defined in claim 18 wherein said stiffener means comprises a second insulation layer and a plurality of second wires encased therein, said second insulation layer and second wires being contained within said first layer, and said econd wires imparting said desired rigidity to said cable means.

20. An apparatus as defined in claim 19 wherein said vent means comprises a channel formed within said second insulation layer.

21. An apparatus as defined in claim 14 wherein said cushion means is disposed at said leading end and extends beyond said transducer means so as to form a soft, resilient means for minimizing damage to adjacent tissue.

22. A disposable intracompartmental pressure transducer apparatus, comprising:
   a dielectric substrate, said substrate having a hole formed therethrough;
   a semiconductor pressure transducer having a pressure diaphragm with first and second sides, the pressure transducer being mounted on said substrate such that the first side of the pressure diaphragm is positioned over said hole in the substrate;
   a cap positioned over the pressure transducer and secured to the substrate so as to enclose the second side of the pressure diaphragm, the cap having a vent hole formed through a side thereof;
   a flexible boot encapsulating said substrate, said transducer and said cap therewithin, said booth having a hole formed therein in alignment with said hole of said substrate;
   a dielectric material used to fill the holes in said boot and substrate so as to be in contact with said first side of the pressure diaphragm, said dielectric material communicating pressure pulses to the first side of the pressure diaphragm;
   a stylet having a vent space formed therethrough, one end of the stylet being bonded to the cap such that the vent space through the stylet communicates with the vent hole through the side of the cap;
   a cable enclosing the stylet and having a plurality of wires electrically connected to the pressure transducer, said boot and said transducer being mounted at an end of said cable to permit insertion thereof into a body compartment; and
   a plug connected to the cable at the other end thereof, the plug having a channel formed therethrough in communication with the vent space formed through the stylet, said channel of the plug terminating at one end in a hole formed in a side of the plug.

* * * * *

UNITED STATES PATENT AND TRADEMARK OFFICE
CERTIFICATE OF CORRECTION

PATENT NO. : 4,785,822

DATED : November 22, 1988

INVENTOR(S) : William D. Wallace

It is certified that error appears in the above-identified patent and that said Letters Patent is hereby corrected as shown below:

```
Column 1, line 30, "held" should be --help--
Column 4, line 56, "to connected" should be --to connect--
Column 4, line 64, "guide tube." should be --a guide tube.--
Column 9, line 44, "apprioximately" should be --approximately--
Column 9, line 47, "preferrably" should be --preferably--
Column 12, line 17, "econd" should be --second--
Column 10, line 38, "premanently" should be --permanently--
```

Signed and Sealed this

Nineteenth Day of September, 1989

Attest:

DONALD J. QUIGG

Attesting Officer

Commissioner of Patents and Trademarks